United States Patent [19]

Jasys

[11] Patent Number: 4,868,297
[45] Date of Patent: Sep. 19, 1989

[54] PROCESS FOR PREPARING SULTAMICILLIN AND ANALOGS

[75] Inventor: Vytautas J. Jasys, New London, Conn.

[73] Assignee: Pfizer Inc., New York, N.Y.

[21] Appl. No.: 916,663

[22] Filed: Oct. 8, 1986

Related U.S. Application Data

[63] Continuation of Ser. No. 466,895, Dec. 6, 1982, abandoned.

[51] Int. Cl.$^4$ ................... C07D 499/10; C07D 499/08
[52] U.S. Cl. .................................. 540/319; 540/310; 540/318
[58] Field of Search ............................... 540/318, 319

[56] References Cited

U.S. PATENT DOCUMENTS

| | | | |
|---|---|---|---|
| 3,325,479 | 6/1967 | Fosker et al. | 540/328 |
| 4,244,951 | 1/1981 | Bigham | 514/195 |
| 4,342,772 | 8/1982 | Godtfredsen et al. | 514/195 |
| 4,393,001 | 6/1983 | Jasys | 540/331 |

*Primary Examiner*—Werren B. Lone
*Assistant Examiner*—Vera C. Clarke
*Attorney, Agent, or Firm*—Peter C. Richardson; J. Trevor Lumb; Robert K. Blackwood

[57] ABSTRACT

6-Halo- and 6,6-dihalo-1,1-dioxopenicillanoyloxymethyl 6-[D-2-(2-alkoxycarbonyl-1-methylvinylamino- and 1-methyl-3-oxo-1-butenylamino)-2-phenylacetamido]penicillanates and analogs; process for their conversion to sultamicillin and analogs; and process for their preparation.

14 Claims, No Drawings

PROCESS FOR PREPARING SULTAMICILLIN AND ANALOGS

This is a continuation of application Ser. No. 446,895, filed on Dec. 6, 1982, now abandoned.

BACKGROUND OF THE INVENTION

The present invention is concerned with intermediates and a process useful in the synthesis of sultamicillin and analogs.

Sultamicillin is the USAN (United States Adopted Name) or so-called generic name for 1,1-dioxopenicillanoyloxymethyl 6-(D-alpha-amino-alpha-phenylacetamido)penicillanate (as named by Godtfredsen et al., U.S. Pat. No. 4,342,772) or 6'-(2-amino-2-phenylacetamido)penicillanoyloxymethyl penicillaanate 1,1-dioxide (as named by Bigham, U.S. Pat. No. 4,244,951). These patents disclose various processes for sultamicillin and analogs, all of which involve the hydrogenolysis or hydrolysis (as appropriate) of an alpha-azido or protected amino group (e.g., benzyloxycarbonylamino, triphenylmethylamino, 2-methoxycarbonyl-1-methylvinyl or dimethylaminocarbonyl-1-methylvinylamino). The Godtfredsen et al. analogs include certain 6-betahalo-1,1-dioxopenicillanoyloxymethyl esters as antibacterial agents. Certain of Godtfredsen's generally disclosed alpha-amino protected, 6-beta-halo precursors also have utility in the present novel process for sultamicillin and analogs. However, in contrast to Godtfredsen et al., the halo group is removed as part of the present novel process.

Jasys has earlier disclosed a related process for sultamicillin and analogs. That process involves hydrogenolysis of 6-halo- and 6,6-dihalo-1,1-dioxopenicillanoyloxymethyl esters wherein the alpha-amino precursor group is azido or a benzyloxycarbonylamino group. See, for example, U.K. patent application No. 2,095,250A having priority to U.S. Pat. Ser. No. 246,456, filed Mar. 23, 1981, now abandoned.

SUMMARY OF THE INVENTION

The present invention is concerned with compounds of the formula

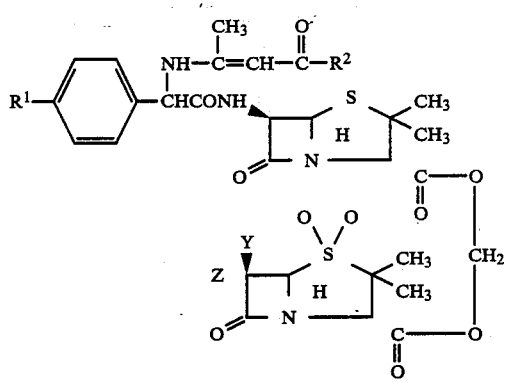

wherein $R^1$ is hydrogen, hydroxy, $(C_2-C_7)$alkanoyloxy, $(C_2-C_7)$alkoxycarbonyloxy, benzoyloxy, or benzyloxy monosubstituted with $(C_1-C_4)$alkyl or $(C_1-C_4)$alkoxy; $R^2$ is methyl or $(C_1-C_3)$alkoxy; Y is hydrogen, Cl, Br or I; and Z is Cl, Br or I.

These compounds are useful as intermediates in the synthesis of sultamicillin and its analogs. Preferred compounds have Y as hydrogen and Z as Br or particularly both Y and Z as Br. The preferred value of $R^2$ is methoxy; and the preferred value of $R^1$ are hydrogen, hydroxy and acetoxy. The most highly preferred compounds are sultamicillin precursors, particularly those where Y and Z are both Br and $R^2$ is $(C_1-C_3)$alkoxy, most particularly methoxy.

The present invention also encompasses a process for the preparation of a compound of the formula

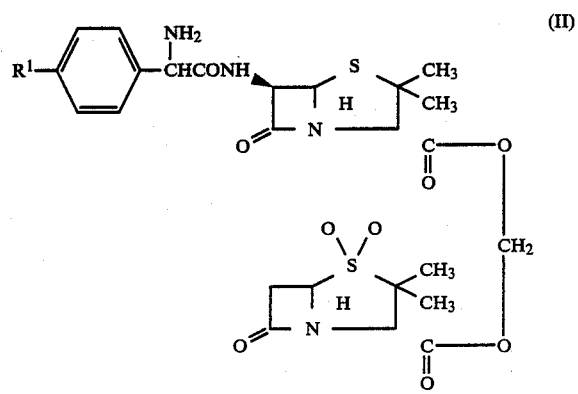

wherein $R^1$ is as defined above. (When $R^1$ is hydrogen, the compound prepared is sultamicillin.) This process is characterized by contacting with hydrogen, in the presence of a noble metal catalyst in a reaction-inert solvent, a compound of the formula

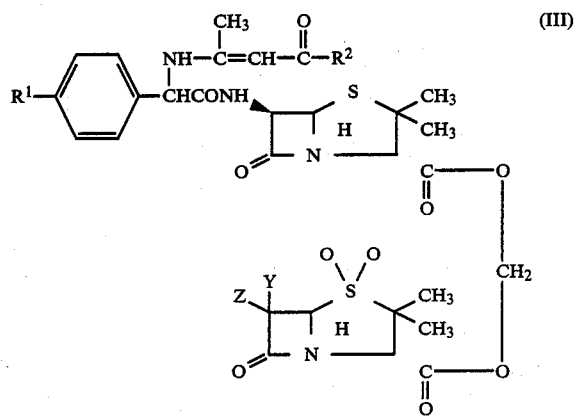

wherein $R^1$, $R^2$, Y and Z are defined above. It will be noted that the compounds of formula (III) correspond to the compounds of formula (I), except that the monohalo compounds are not longer restricted to 6-alpha stereochemistry. The preferred noble metal catalyst is palladium.

As used herein, the expression "reaction-inert solvent" refers to a solvent which does not interact with reagents, intermediates or products in a manner which adversely affects the yield of the desired product.

The process of the present invention is further characterized by preparation of the compound of the formula (III) by reacting in a reaction-inert solvent the tetrabutylammonium salt of a compound of the formula

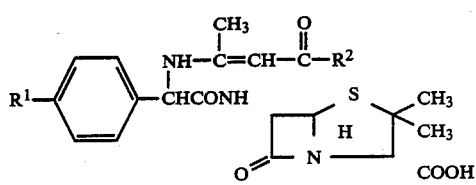

wherein $R^1$ and $R^2$ are as defined above, with the iodomethyl ester of a compound of the formula

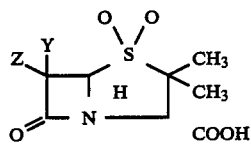

wherein Y and Z are as defined above; or conversely the iodomethyl ester of a compound of the formula (IV) with the tetrabutylammonium salt of a compound of the formula (V).

DETAILED DESCRIPTION OF THE INVENTION

The catalytic hydrogenation of the present invention, converting compounds of the formula (III) to compounds of the formula (II), is readily performed. Accordingly, a compound of the formula (III), as defined above, is dissolved or suspended in a reaction-inert solvent medium in the presence of a catalytic amount of a noble metal catalyst and agitated under hydrogen at an appropriate temperature and pressure until reduction to the compound of the formula (II), as defined above, is substantially complete. Thereafter, the noble metal catalyst and the product are recovered and the product purified by conventional procedures.

Suitable reaction-inert solvents for the present hydrogenation include water and a variety of organic solvents, or mixtures thereof. An excess of acid or base is generally avoided, particularly in the presence of water, in order to avoid hydrolysis of the relatively sensitive methanediol ester and beta-lactam linkages. Suitable solvents include lower alcohols such as 2-propanol or 2-butanol, ethers (particularly more polar ethers such as tetrahydrofuran, dioxane, 1,2-dimethoxyethane and the like), hydrocarbons (particularly aromatic hydrocarbons) and halogenated hydrocarbons (methylene chloride, chloroform, dichlorobenzene and the like). Organic solvents are preferred. A mixture of methylene chloride and 2-propanol represents a solvent system particularly well-suited for the present hydrogenation.

The temperature is no more critical in the present process than it is in other known hydrogenations of penicillin antibiotics. Thus the preferred temperature range is from about 0° to 60° C., more preferably in the lower half of this range. Such lower temperatures minimize degradation, but are not so low that reaction rate is inordinately slow. Ambient temperatures (about 16°-27° C.) are particularly well-suited.

The pressure employed in the hydrogenation is also not critical, and can range from subatmospheric to 100 atmospheres or more. On a commercial scale, moderate pressures (e.g. 3-8 atmospheres) are preferred, since at such pressures the hydrogenation will generally occur at a reasonable rate, without an excessive level of catalyst, using relatively less sophisticated and expensive equipment. In some cases, where the level of catalyst is significantly reduced by using higher pressures, simple economics will dictate the preferred use of higher pressures and high pressure equipment.

The noble metal catalysts as employed in the present process include palladium, rhodium and platinum, either of the supported or non-supported type, as well as the known catalytic compounds thereof such as the oxides or chlorides. Examples of suitable catalyst supports include carbon, silica, barium carbonate, and the like. The catalyst can be preformed or formed in situ by reduction of an appropriate salt. Examples of the preferred palladium catalyst are palladium chloride, palladium on calcium carbonate or most particulary palladium (e.g. 5-10% by weight) on carbon.

The expression "catalytic amount" as used herein is well understood by those skilled in the art of known penicillin hydrogenation. As usual, the amount of catalyst required will vary with the particular type and batch of catalyst and the purity of the particular reagents, as well as the particular container, type of agitation, amount of void space, temperature and pressure employed. Under a particular set of conditions, the optimal amount of a particular catalyst can readily be determined by routine experimentation.

The intermediate compounds of the formula (III) used in the process of the present invention are readily prepared by reaction of an appropriate halomethyl ester with an appropriate carboxylate salt. The preferred halomethyl ester is the iodomethyl ester; while the preferred salt is a quaternary lower alkyl ammonium salt, particularly the tetrabutylammonium salt. The reaction is carried out in a reaction-inert solvent, preferably a polar organic solvent such as dimethylformamide. Suitable and preferred temperature ranges are the same as those detailed above for the hydrogenation process. The required iodomethyl ester and tetrabutylammonium salts are prepared according to methods as specifically exemplified below from well-known and readily available starting materials.

The present invention is illustrated by the following Examples. However, it should be understood that the invention is not limited to the specific details of these Examples. $^1$H-nmr delta values are relative to TMS (tetramethylsilane).

PREPARATION 1

6,6-Dibromopenicillanic Acid

To 500 ml of dichloromethane cooled to 5° C. was added 119.9 g of bromine, 200 ml of 2.5N sulfuric acid and 34.5 g of sodium nitrite. To this stirred mixture was then added 54.0 g of 6-aminopenicillanic acid, portionwise over 30 minutes, with the temperature maintained from 4° to 10° C. Stirring was continued for 30 minutes at 5° C., and then 410 ml of a 1.0M solution of sodium bisulfite was added dropwise at 5° to 10° C. during 20 minutes. The layers were separated and the aqueous layer was extracted twice with 150 ml of dichloromethane. The original dichloromethane layer was combined with the two extracts to give a solution of 6,6-dibromopenicillanic acid. This solution was used directly in preparation of esters or evaporated to dryness to provide the desired product.

PREPARATION 2

6-Chloro-6-iodopenicillanic Acid

To 100 ml of dichloromethane cooled to 3° C. was added 4.87 g of iodine chloride, 10 ml of 2.5N sulfuric acid and 2.76 g of sodium nitrite. To this stirred mixture was then added 4.32 g of 6-aminopenicillanic acid portionwise during a 15 minute period. Stirring was continued for 20 minutes at 0°-5° C., and then 100 ml of 10% sodium bisulfite solution was added dropwise at ca. 4° C. Stirring was continued for 5 minutes and the the layers were separated. The aqueous layer was extracted with dichloromethane (2×50 ml) and the combined dichloromethane solutions were washed with brine, dried (MgSO$_4$) and evaporated in vacuo to give the title compound as a tan solid, m.p. 148°-152° C.; $^1$H-nmr (CDCl$_3$) delta 5.40 (s, 1H), 4.56 (s, 1H), 1.67 (s, 3H) and 1.50 (s, 3H) ppm; ir (KBr disc) 1780 and 1715 cm$^{-1}$.

PREPARATION 3

6-Bromo-6-iodopenicillanic Acid

To 100 ml of dichloromethane, cooled to 5° C., was added 10 ml of 2.5N sulfuric acid, 6.21 g of iodine bromide and 2.76 g of sodium nitrite. To this mixture was added, with vigorous stirring, at 0°-5° C., over 15 minutes, 4.32 g of 6-aminopenicillanic acid. Stirring was continued for a further 20 minutes at 0°-5° C., and then 100 ml of 10% sodium bisulfite was added dropwise between 0° and 10° C. At this point, the layers were separated and the aqueous layer was extracted with dichloromethane (3×50 ml). The combined dichloromethane layers were washed with brine, dried (MgSO$_4$) and evaporated in vacuo. The residue was dried under high vacuum for 30 minutes to give 6.0 g (72% yield) of the title compound m.p. 144°-147° C.; $^1$H-nmr (CDCl$_3$) delta 5.50 (s, 1H), 4.53 (s, 1H), 1.70 (s, 3H) and 1.53 (s, 3H) ppm; ir (KBr disc) 1785 and 1710 cm$^{-1}$; m/e=406.

6-Chloro-6-bromopenicillanic acid is prepared from 6-aminopenicillanic acid via diazotization followed by reaction with bromine chloride, according to the same procedure.

EXAMPLE 1

Chloromethyl 6,6-Dibromopenicillanate 6,6-Dibromopenicillanic acid (8.0 g, 22 mmole) was stirred with 75 ml methylene chloride, and then 35 ml water was added. To this was added sufficient tetrabutylammonium hydroxide to adjust to pH 8. The organic layer was separated, the aqueous phase extracted with 30 ml methylene chloride. The combined organic layers were evaporated to dryness in vacuo to provide the tetrabutylammonium salt of 6,6-dibromopenicillanic acid, 14.2 g, as a light brown oil. To this was added 40 ml of chloroiodomethane, and the resulting mixture stirred under nitrogen for three hours at room temperature. The reaction mixture was concentrated in vacuo, the residue stored overnight at room temperature and purified by chromatography on 300 g silica gel, eluting with 95:5 (by volume) toluene/ethyl acetate. Fractions containing the less polar material were combined and evaporated to afford 5.4 g (59%) of the desired product, mp 105°-106° C.; $^1$H-nmr (CDCl$_3$) ppm (delta): 1.6 (s, 3H), 1.75 (s, 3H), 4.62 (s, 1H), 5.8 (dd, 2H), 5.82 (s, 1H).

Employing the appropriate 6-substituted or 6,6-disubstituted penicillanic acid, the following esters are likewise prepared:
chloromethyl 6-chloro-6-iodopenicillanate;
chloromethyl 6-bromo-6-iodopenicillanate;
chloromethyl 6-chloro-6-bromopenicillanate; and
chloromethyl 6-beta-bromopenicillanate 1,1-dioxide.

EXAMPLE 2

Iodomethyl 6,6-Dibromopenicillanate

To 25 ml of acetone was added 4.15 g (10.2 mmole) chloromethyl 6,6-dibromopenicillanic acid and 7.5 g (50 mmole) sodium iodide. The mixture was stirred overnight at room temperature and the acetone was evaporated to afford a dark residue. This was dissolved in 150 ml ethyl acetate, washed with water (3×25 ml), saturated brine (25 ml), dried (MgSO$_4$) and the solvent evaporated in vacuo to yield a residual oil which was purified by chromatography on 100 g silica gel, eluting with 1:1 (by volume) ethyl acetate/hexane. Thirty milliliter fractions were collected. The product eluted in fractions 4-6, which were combined and evaporated to afford 5.95 g of colorless oil which crystallized upon standing, mp 67°-68° C. $^1$H-nmr (CDCl$_3$) ppm (delta): 1.55 (s, 3H), 1.65 (s, 3H), 4.54 (s, 1H), 5.8 (s, 1H), 5.98 (s, 2H).

In like manner, the other chloromethyl esters of the preceding Example are converted to the corresponding iodomethyl esters.

EXAMPLE 3

Chloromethyl 6,6-Dibromopenicillanate 1,1-Dioxide

A solution of 7.1 g (17.4 mmole) chloromethyl 6,6-dibromopenicillanate in 75 ml ethyl acetate was cooled to 0° C. and 7.3 g (36 mmole) of m-chloroperbenzoic acid was added. The mixture was stirred under nitrogen at 0° C. overnight, diluted to 150 ml with ethyl acetate, and 50 ml water added at 0° C. Sufficient sodium bisulfite was added to destroy the excess peracid, the mixture adjusted from pH 2 to pH 7.5 with sodium bicarbonate, the organic layer separated and washed with 50 ml saturated sodium bicarbonate, 50 ml water and 25 ml brine. The washed extracts were dried (MgSO$_4$), concentrated to dryness in vacuo and the residue purified by chromatography on 300 g silica gel, eluting with 9:1 (by volume) toluene/hexane to afford 5.0 g (65%) of the desired dioxide as a crystalline solid, mp 95°-96° C. $^1$H-nmr (CDCl$_3$) ppm (delta): 1.5 (s, 3H), 1.7 (s, 3H), 4.58 (s, 1H), 5.04 (s, 1H), 5.8 (dd, 2H).

Analysis: Calculated for C$_9$H$_{10}$NO$_5$SBr$_2$Cl: C, 24.59; H, 2.29; N, 3.18 Found: C, 24.63; H, 2.49; N, 3.31.

A second, more polar component was isolated from the chromatography column, 0.8 g. This was identified as a 9:1 mixture of the alpha- and beta-sulfoxides of chloromethyl 6,6-dibromopenicillanate by $^1$H-nmr.

EXAMPLE 4

Iodomethyl 6,6-Dibromopenicillanate 1,1-Dioxide

To 40 ml of acetone was added 0.25 g (0.5 mmole) iodomethyl 6,6-dibromopenicillanate and the mixture stirred until a solution was obtained. Water (10 ml) was then added, followed by sufficient concentrated phosphoric acid to adjust the mixture to pH 4.0. Then 158 mg (1 mmole) powdered potassium permanganate was added and the mixture stirred at room temperature for 1.25 hours. Ethyl acetate, 100 ml and water, 50 ml, were added. The resulting mixture was adjusted to pH 2.0 with 6N hydrochloric acid and sodium bisulfite added to consume the excess oxidizing agent (pH 2.9). The organic layer was separated, the aqueous phase extracted with 50 ml ethyl acetate and the combined organic layers were washed with saturated brine (3×25 ml). After drying over anhydrous sodium sulfate and evaporation of solvent, 0.29 g of colorless oil was obtained. The oil was purified by chromatography on 25 g of silica gel eluting with 1:1 ethyl acetate/hexane taking 15 ml fractions. Fractions 4 and 5 were combined and evaporated in vacuo to yield 0.27 g (100%) of colorless oil which crystallized upon standing, mp 71°–73° C. $^1$H-nmr (CDCl$_3$) ppm (delta): 1.5 (s, 3H), 1.62 (s, 3H), 4.49 (s, 1H), 5.02 (s, 1H), 5.98 (dd, 2H).

The other iodomethyl esters of Example 2 are converted to the corresponding 1,1-dioxides in like manner.

EXAMPLE 5

Iodomethyl 6-alpha-Bromopenicillanate 1,1-Dioxide

Attempts to prepare iodomethyl 6,6-dibromopenicillanate 1,1-dioxide from the chloromethyl ester prepared in Example 3, by treatment with sodium iodide in acetone by the procedure of Example 2 gave iodomethyl 6-alpha-bromopenicillanate 1,1-dioxide. $^1$H-nmr (CDCl$_3$) ppm/delta: 1.55 (s, 3H), 1.70 (s, 3H), 4.43 (s, 1H), 5.2 (d, 1H), 5.75 (d, 1H), 6.0 (dd, 2H).

EXAMPLE 6

Iodomethyl 6-beta-Bromopenicillanate 1,1-Dioxide

A solution of 0.12 g (0.33 mmole) chloromethyl 6-beta-bromopenicillanate 1,1-dioxide and 0.25 g (1.66 mmole) sodium iodide in 5 ml of acetone was stirred 30 hours at room temperature. The resulting pale yellow suspension was evaporated to dryness and the residue taken up in 50 ml of ethyl acetate, washed successively with 2×10 ml water, 10 ml saturated brine and dried over anhydrous sodium sulfate. The resulting solution was evaporated at reduced pressure to obtain the title compound, as a solid, 0.14 g. $^1$H-nmr (CDCl$_3$) ppm (delta): 1.45 (s, 3H), 1.65 (s, 3H), 4.5 (s, 1H), 4.83 (d, 1H), 5.42 (d, 1H), 6.0 (dd, 2H).

EXAMPLE 7

6-beta-Chloropenicillanic Acid 1,1-Dioxide

An oxidizing solution was prepared from 185 mg of potassium permanganate, 0.063 ml of 85% phosphoric acid and 5 ml of water. This oxidizing solution was added dropwise to a solution of 150 mg of sodium 6-beta-chloropenicillanate in 5 ml of water at 0°–5° C., until the purple color of the potassium permanganate persisted. Approximately half of the oxidizing solution was required. At this point, the potassium permanganate color was discharged by the addition of solid sodium bisulfite, and then the reaction mixture was filtered. Ethyl acetate was added to the filtrate and the pH was adjusted to 1.8. The layers were separated and the aqueous layer was further extracted with ethyl acetate. The combined ethyl acetate layers were washed with water, dried and evaporated in vacuo to give 118 mg of the title compound. $^1$H-nmr (CD$_3$COCD$_3$) delta 5.82 (d, 1H), 5.24 (d, 1H), 4.53 (s, 1H), 1.62 (s, 3H) and 1.50 (s, 3H) ppm.

By the procedure of Examples 1 and 2, the present product is converted, via the corresponding chloromethyl ester, to the corresponding iodomethyl ester.

EXAMPLE 8

Tetrabutylammonium 6-[D-2-(2-Methoxycarbonyl-1-methylvinylamino)-2-phenylacetamido]penicillanate Tetrabutylammonium hydrogen sulfate (33.9 g, 0.10 mole) and 50 ml of 2N NaOH were combined with 200 ml H$_2$O. The resulting pH was about 6.8. With stirring, CH$_2$Cl$_2$ (300 ml) and then ampicillin trihydrate (33.9 g, 0.10 mole) were added, and the pH adjusted from 4.5 to 8.5 with 53 ml 2N NaOH. The layers were separated and the aqueous layer extracted 4×200 ml CH$_2$Cl$_2$. The five organic layers were combined and evaporated to dryness in vacuo to yield the tetrabutylammonium salt of ampicillin, 54.1 g, 91.7%. Methyl acetoacetate (200 ml) was added to the salt and the water formed in the reaction removed by evaporation using a bath at 35° and a pressure of 5 mm. After one hour, title product began to crystallize. After 1.75 hour, 600 ml of ethyl acetate and 200 ml of hexane were added. After cooling to 0°–5°, title product was recovered by filtration, 53.5 g, 84.8% from salt, 77.8% overall from ampicillin; $^1$H-nmr (CDCl$_3$) delta: 7.2 (m), 5.6–5.0 (m), 4.5 (s), 4.2 (s), 3.55 (s), 3.4–2.9 (m), 1.8 (s), 1.7–0.8 (m).

In like manner, substituting ethyl acetoacetate or acetylacetone for methyl acetoacetate, the following compounds are prepared:

tetrabutylammonium 6-[D-2-(2-ethoxycarbonyl-1-methylvinylamino)-2-phenylacetamido]penicillanate; and tetrabutylammonium 6-[D-2-(1-methyl-3-oxo-1-butenylamino)-2-phenylacetamido]penicillanate.

EXAMPLE 9

Tetrabutylammonium 6-[2-(1-Methyl-2-methoxycarbonylvinylamino)-2-(4-hydroxyphenyl)acetamido]penicillanate To 300 ml of dichloromethane was added 41.9 g of 6-(2-amino-2-[4-hydroxyphenyl]acetamido)penicillanic acid trihydrate and 50 ml of water, and then the pH was adjusted to 8.5 using 40% aqueous tetrabutylammonium hydroxide. Three layers were obtained. The upper layer was removed, saturated with sodium sulfate and then it was extracted with dichloromethane. The extracts were combined with the middle layer and the lower layer, and the resulting mixture was evaporated in vacuo to give an oil which crystallized on trituration with acetone. This afforded 44.6 g of tetrabutylammonium 6-(2-amino-2-[4-hydroxyphenyl]acetamido)penicillanate.

The above salt was added to 150 ml of methyl acetoacetate and the suspension was heated at ca. 65° C. until a clear solution was obtained (8 minutes). The mixture was allowed to cool, and then the solid was recovered by filtration. The solid was washed with methyl acetoacetate, followed by diethyl ether, to give 49.25 g of title product.

In like manner, substituting the appropriate acylamoxicillin for amoxicillin, the following compounds are prepared:

tetrabutylammonium 6-[D-2-(2-methoxycarbonyl-1-methylvinylamino)-2-(p-acetoxypheny)acetamido]-penicillanate;

tetrabutylammonium 6-[D-2-(2-methoxycarbonyl-1-methylvinylamino)-2-(p-benzoyloxyphenyl)acetamdio]-penicillanate; and tetrabutylammonium 6-[D-2-(2-methoxycarbonyl-1-methylvinylamino)-2-(p-ethoxycarbonyloxyphenyl)acetamido]penicillanate.

EXAMPLE 10

6,6-Dibromo-1,1-dioxopenicillanoyloxymethyl 6-[D-2-(2-Methoxycarbonyl-1-methylvinyl)-2-phenylacetamido]penicillanate Title product of Example 2 (10.1 g, 0.019 mole) was dissolved in 135 ml dry dimethylformamide (DMF). Title product of Example 8 (19.6 g, 0.029 mole) was separately dissolved in 50 ml dry DMF and added to the first solution and the mixture stirred one hour at room temperature, by which time silica gel tlc with 1:1 ethyl acetate:hexane as eluant indicated consumption of starting material ($R_f$ 0.6). The reaction mixture was poured into 1500 ml ethyl acetate and 500 ml $H_2O$. The layers were separated and the aqueous layer extracted with 100 ml fresh ethyl acetate. The organic layers were combined, washed 4×250 ml $H_2O$ and 2×250 ml brine, dried ($MgSO_4$) and stripped to yield title product as a yellow foam, 6.7 g, 41%; $^1$H-nmr/DMSO-$d_6$/delta: 1.4–1.8 (12H, m), 1.9 (3H, s), 3.7 (3H, s), 4.45–4.7 (3H, m), 5.2 (1H, s), 5.4–5.8 (3H, m), 6.0 (2H, s), 7.5 (5H, s), 9.2–9.7 (2H, m).

In like manner, other iodomethyl 6-halo and 6,6-dihalopenicillanate 1,1-dioxides and ampicillin/amoxicillin enamines of preceding Examples are reacted to form the corresponding 6,6-dibromo-1,1-dioxopenicillanoyloxymethyl, 6-chloro-6-iodo-1,1-dioxopenicillanoyloxymethyl, 6-bromo-6-iodo-1,1-dioxopenicillanoyloxymethyl, 6-chloro-6-bromo-1,1-dioxopenicillanoyloxymethyl, 6-beta-bromo-1,1-dioxopenicillanoyloxymethyl, 6-alpha-bromo-1,1-dioxopenicillanoyloxymethyl and 6-beta-chloro-1,1-dioxopenicillanoyloxymethyl 6-[D-2-(2-methoxycarbonyl-1-methylvinylamino)-2-phenylacetamido]penicillanates, 6-[D-2-(2-ethoxycarbonyl-1-methylvinylamino)-2-phenylacetamido]penicillanates, 6-[D-2-(1-methyl-3-oxo-1-butenylamino)-2-phenylacetamido]penicillanates, 6-[D-2-(2-methoxycarbonyl-1-methylvinylamino)-2-(p-hydroxyphenyl)acetamido]penicillanates, 6-[D-2-(2-methoxycarbonyl-1-methylvinylamino)-2-(p-acetoxyphenyl)acetamido]penicillanates, 6-[D-2-(2-methoxycarbonyl-1-methylvinylamino)-2-(p-benzoyloxyphenyl)acetamido]penicillanates, and 6-[D-2-(2-methoxycarbonyl-1-methylvinylamino)-2-(p-ethoxycarbonyloxyphenyl)acetamido]penicillanates.

EXAMPLE 11

1,1-Dioxopenicillanoyloxymethyl 6-(D-2-Amino-2-phenylacetamido)penicillanate

Title product of the preceding Example (1.7 g, 2 mmoles) was dissolved in 120 ml 1:1 $CH_2Cl_2$:isopropanol. 5% Pd/C (4.3 g) was added and the mixture hydrogenated at 50 psig for one hour. Catalyst was recovered by filtration over diatomaceous earth and the mother liquor stripped in vacuo to yield title product as the hydrobromide salt, 820 mg, 57%; $^1$H-nmr (DMSO-$d_6$) delta: 7.5 (m), 6.2 (s), 5.7 (m), 5.6 (d), 5.3 (m), 5.2 (s), 3.8 (q), 3.5 (m, 1.5 (d).

Particularly on a large scale, the present hydrogenation is preferably carried out in the presence of one equivalent of $NaHCO_3$ or 1–2 equivalents of pyridine.

By the same method the other esters of the preceding Example are converted to hydrochloride and/or hydrobromide salts of the same title product, or to 1,1-dioxopenicillanoyloxymethyl 6-[D-2-amino-2-(p-hydroxyphenyl)acetamido]penicillanate, 6-[D-2-amino-2-(p-acetoxyphenyl)acetamido]penicillanate, 6-[D-2-amino-2-(p-benzoyloxyphenyl)acetamido]penicillanate, or 6-[D-2-amino-2-(p-ethoxycarbonyloxyphenyl)acetamido]penicillanate.

I claim:

1. A process for the preparation of a compound of the formula

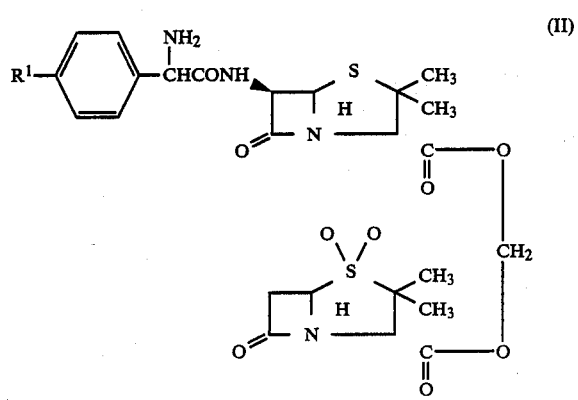

(II)

wherein $R^1$ is hydrogen, hydroxy, ($C_2$–$C_7$)alkanoyloxy, ($C_2$–$C_7$)alkoxycarbonyloxy, benzoyloxy, or benzoyloxy monosubstituted with ($C_1$–$C_4$)alkyl or ($C_1$–$C_4$)alkoxy; or a pharmaceutically acceptable acid addition salt thereof; which is characterized by contacting a compound of the formula

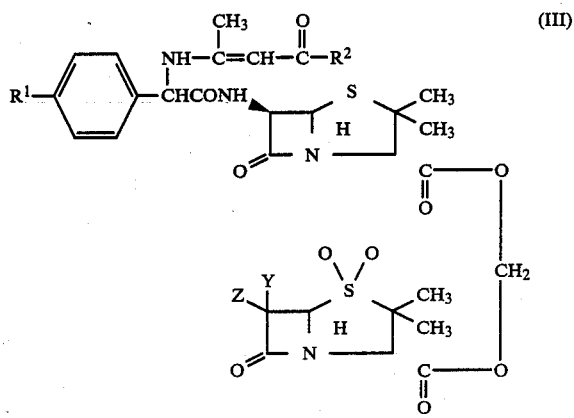

(III)

wherein
wherein $R^1$ is hydrogen, hydroxy, ($C_2$–$C_7$)alkanoyloxy, ($C_2$–$C_7$)alkoxycarbonyloxy, benzoyloxy, or benzoyloxy monosubstituted with ($C_1$–$C_4$)alkyl or ($C_1$–$C_4$)alkoxy;
$R^2$ is methyl or ($C_1$–$C_3$)alkoxy;
Y is hydrogen, Cl, Br or I; and
Z is Cl, Br or I;
with hydrogen in the presence of a noble metal catalyst in a reaction inert solvent.

2. A process of claim 1 wherein Y and Z are each Br.
3. A process of claim 1 wherein $R^2$ is methyl.
4. A process of claim 1 wherein $R^2$ is ($C_1$–$C_3$)alkoxy.
5. A process of claim 1 wherein $R^1$ is hydroxy or acetoxy.
6. A process of claim 1 wherein $R^1$ is hydrogen.
7. A process of claim 6 wherein Y and Z are each Br.
8. A process of claim 6 wherein $R^2$ is ($C_1$–$C_3$)alkoxy.

9. A process of claim 8 wherein Y and Z are each Br.

10. A process of claim 9 wherein $R^2$ is methoxy.

11. A process of claim 1 wherein the noble metal catalyst is palladium.

12. A process of claim 9 wherein the noble metal catalyst is palladium.

13. A process of claim 10 wherein the noble metal catalyst is palladium.

14. A process of claim 1 which is further characterized by preparation of the compound of the formula (III) by reaction in a reaction-inert solvent the tetrabutylammonium salt of a compound of the formula

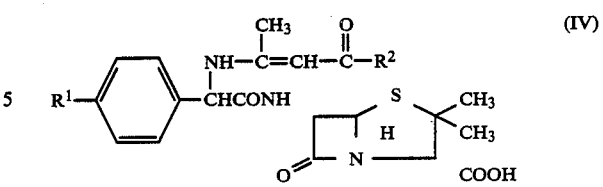

wherein
$R^1$ is hydrogen, hydroxy, $(C_2-C_7)$alkanoyloxy, $(C_2-C_7)$alkoxycarbonyloxy, benzoyloxy, or benzoyloxy monosubstituted with $(C_1-C_4)$alkyl or $(C_1-C_4)$alkoxy; and
$R^2$ is methyl or $(C_1-C_3)$alkoxy; with the iodomethyl ester of a compound of the formula

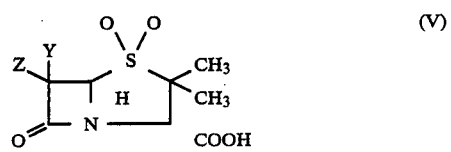

wherein Y is hydrogen, Cl, Br or I and Z is Cl, Br or I; or conversely reacting the iodomethyl ester of a compound of the formula (IV) with the tetrabutylammonium salt of a compound of the formula (V).

* * * * *

UNITED STATES PATENT AND TRADEMARK OFFICE
CERTIFICATE OF CORRECTION

PATENT NO. : 4,868,297
DATED : September 19, 1989
INVENTOR(S) : Vytautus J. Jasys It is certified that error appears in the above-identified patent and that said Letters Patent is hereby corrected as shown below:

Column 1, lines 51 and 57, column 2, lines 17, 25, 40, and 48, column 3, lines 5 and 17, column 10, lines 15, 23, 40 and 47, and column 12, lines 7 and 22, insert a line between the bicyclic group and the group $\underset{O}{\overset{\|}{C}}-$ .

Column 3, line 5 and column 12, line 5, insert the line between the group $-\overset{|}{C}HCONH$ and the bicyclic group.

Signed and Sealed this

Thirteenth Day of December, 1994

Attest:

BRUCE LEHMAN

*Attesting Officer*  *Commissioner of Patents and Trademarks*